(12) United States Patent
Giselbrecht et al.

(10) Patent No.: US 7,858,381 B2
(45) Date of Patent: Dec. 28, 2010

(54) PROCESS FOR PREPARING HIGH-PURITY, HALOGEN-FREE O-PHTHALADEHYDE

(75) Inventors: Karlheinz Giselbrecht, Pasching (AT); Klaus Reiter, Linz (AT); Rudolf Hermanseder, Pennewang (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 841 days.

(21) Appl. No.: 11/475,086

(22) Filed: Jun. 27, 2006

(65) Prior Publication Data

US 2006/0293542 A1 Dec. 28, 2006

(30) Foreign Application Priority Data

Jun. 28, 2005 (AT) ............................. A 1087/2005

(51) Int. Cl.
*G01N 33/00* (2006.01)
(52) U.S. Cl. ...................... 436/128; 568/425; 568/430; 568/345
(58) Field of Classification Search ................. 436/128; 568/345, 425, 430
See application file for complete search history.

(56) References Cited

U.S. PATENT DOCUMENTS 5,107,032 A 4/1992 Erb et al.

5,874,637 A * 2/1999 Giselbrecht et al. ......... 568/430

FOREIGN PATENT DOCUMENTS

EP 0 003 230 8/1979
EP 0 839 789 5/1998

OTHER PUBLICATIONS

HeiLongJiang Medical Journal, vol. 11, No. 1, 1998, p. 6 (translation).

* cited by examiner

*Primary Examiner*—Yelena G Gakh
*Assistant Examiner*—David Weisz
(74) *Attorney, Agent, or Firm*—Nixon & Vanderhye P.C.

(57) ABSTRACT

Improved process for preparing high-purity, halogen-free o-phthalaldehyde, in which
a) tetrahalo-o-xylene is hydrolyzed at a temperature of 155-160° C. and a pressure of from 2 to 5 bar, where appropriate in the presence of a phase-transfer catalyst, to o-phthalaldehyde, which
b) is converted in an acidic alcoholic solution at a temperature of from 0 to the reflux temperature into the corresponding dialkoxyphthalane and, subsequently,
c) an acetal cleavage is effected by acid hydrolysis at a pH >1.5 to pH 7, resulting in high-purity, halogen-free o-phthalaldehyde.

5 Claims, No Drawings

PROCESS FOR PREPARING HIGH-PURITY, HALOGEN-FREE O-PHTHALADEHYDE

Phthalaldehydes such as o-phthalaldehyde (OPA) are used in many areas for example as intermediates for preparing dyes, optical brighteners or specific polymers, in the biocide or photographic industry, and for synthesizing pharmaceutical chemicals. Several process variants have for this reason been described. Thus, o-phthalaldehyde (OPA) can for example according to EP-B-0 147 593 be obtained by ozonolysis of naphthalene in methanol and catalytic reduction of the peroxides produced thereby, with subsequent extraction or crystallization. The disadvantage of this process is that the ester which is formed as byproduct can be separated from OPA only with difficulty and inadequately.

OPA is moreover a reactive compound which is thermally and oxidatively unstable and which on prolonged storage is prone to caking, thus making time-consuming dissolving processes necessary, which may possibly lead to discoloration of OPA. A possibility described in EP-A1-0522312 for protecting the aldehyde from unwanted reactions is to employ o-phthalaldehyde tetraalkyl acetals prepared by electrochemical oxidation as storage compounds.

EP-B-0 839 789 further discloses the conversion of OPA by acid-catalyzed acetal formation with subsequent distillation into a suitable storage compound such as, for instance, into a dialkoxyphthalane or tetraalkyl acetal, from which crude OPA with purities of more than 99.5% is obtained if required after complete acetal cleavage by acid hydrolysis.

However, crude OPA, for example prepared according to EP-B-0 839 789, has a reddish orange color, subsequent recrystallization is also necessary after decolorization with, for example, activated carbon or Tonsil.

The fine OPA powder with a melting point of 57° C. which is obtained by crystallization is likewise prone to blocking. In addition, different batches do not show a constant color and quality.

U.S. Pat. No. 5,107,032 discloses the preparation of OPA by preparing a tetrahalo-o-xylene with subsequent hydrolysis at 90 to 146° C. This entails for example tetrachloro-o-xylene being hydrolyzed with sodium acetate in aqueous acetic acid at a maximum of 146° C. and 3.5 bar, after which toluene extraction 5 times and subsequent distillation of the combined organic phases gives an 87% yield of OPA. However, the disadvantage of this process is, inter alia, that the resulting product is not halogen-free.

It was therefore an object of the present invention to find an improved process for preparing high-purity, halogen-free OPA.

It has unexpectedly been possible to achieve this object by hydrolyzing tetrahalo-o-xylene at elevated temperature above 155° C., subsequent acetalization to the corresponding o-phthalaldehyde acetal, purification of the acetal by distillation, and acetal cleavage at pH >1.5.

The invention accordingly relates to an improved process for preparing high-purity, halogen-free o-phthalaldehyde, which comprises a) hydrolyzing tetrahalo-o-xylene at a temperature of 155-160° C. and a pressure of from 2 to 5 bar, where appropriate in the presence of a phase-transfer catalyst, to o-phthalaldehyde, which b) is converted in an acidic alcoholic solution at a temperature of from 0 to the reflux temperature into the corresponding dialkoxyphthalane and, subsequently, c) an acetal cleavage is effected by acid hydrolysis at a pH >1.5 to pH 7, resulting in high-purity, halogen-free o-phthalaldehyde.

High-purity, halogen-free o-phthalaldehyde (OPA) is prepared in the process of the invention.

The starting material is a tetrahalo-o-xylene. Suitable tetrahalo-o-xylenes are for example those of the formula

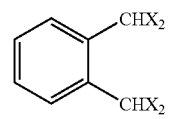

(I)

in which X can be Cl, Br or I.

The tetrahalo-o-xylene (THX) may moreover optionally be substituted one or more times by suitable radicals. Examples of suitable radicals are $C_1$-$C_4$-alkyl, $C_5$-$C_{20}$-aryl, OH, $NO_2$, CN, Cl, Br or $CO_2H$.

Unsubstituted THX compounds are preferably employed, and X is preferably chlorine.

Suitable THX compounds are commercially available (with X equal to Cl or Br) or can be prepared in a known manner, for example by reacting o-xylene with elemental chlorine with exposure to light or with the aid of free radical initiators such as AIBN, $PCl_3$, and dibenzoyl peroxide etc.

A THX is hydrolyzed according to the invention at a temperature of 155-160° C. and a pressure of from 2 to 5 bar, preferably 3 to 4 bar, to the corresponding o-phthalaldehyde.

The hydrolysis is carried out in an aqueous system composed of $C_1$-$C_4$-carboxylic acid in the presence of a base such as, for instance, NaOH, LiOH, KOH, etc. It is preferred to employ acetic acid in the presence of NaOH (40 to 50% strength).

For this purpose, preferably the carboxylic acid or aqueous carboxylic acid and a THX are mixed, and subsequently the aqueous base and water are added. The sequence of the addition may also vary, however.

The amount of carboxylic acid employed is >4 to 20 mole equivalents based on THX. 8 to 10 mole equivalents based on THX are preferred.

The amount of base employed is from 4.0 to 5.0 mole equivalents based on THX.

It is possible where appropriate to add to the reaction mixture, in order to achieve a higher reaction rate, a phase-transfer catalyst (PTC) (1-5 mol % based on THX).

Suitable PTCs are usual compounds such as, for instance, quaternary ammonium salts and phosphonium salts, for example tetraalkylammonium and tetraalkyl-phosphonium salts or arylalkyltrialkylammonium salts. Preferred salts in this connection are halides. Examples thereof are tetrabutylammonium chloride or bromide, ethyltrioctylphosphonium chloride, benzyltriethylammonium chloride etc.

After the hydrolysis has taken place, the corresponding crude o-phthalaldehyde (OPA) is obtained by extraction with usual extractants such as, for instance, methyl tert-butyl ether, toluene, ethyl acetate, etc, and subsequent distillation of the solvents and extractants.

Subsequently, in step b), the crude OPA is converted into the acetal, the dialkoxyphthalane, in a conventional way by acid-catalyzed acetalization with an alcohol.

The alcohol preferably employed in this case is a $C_1$-$C_4$-alcohol, particularly preferably methanol or ethanol.

The crude OPA is for this purpose dissolved in the alcohol. The solution is then adjusted to a pH of between 0 and 3, preferably between 0.5 and 2, by addition of an acid.

Examples of suitable acids are mineral acids such as, for instance, HCl, $H_2SO_4$, $H_3PO_4$, organic acids such as, for instance, formic acid, acetic acid, p-toluenesulfonic or methanesulfonic acid or acidic ion exchangers.

The temperature in this step is from 0° C. to the reflux temperature, preferably to 50° C.

After the acetalization has taken place, an aqueous alkali is added to the solution to neutralize the acid or acidic organic compounds. NaOH or KOH are suitable for example as alkali.

The alcohol used as solvent is removed by distillation subsequently or simultaneously.

The dialkoxyphthalane is in turn isolated by extraction and subsequent distillation. The isolated OPA acetals are in this case obtained in very high, halogen-free quality (>99.5 GC area %) and in very high yield of up to more than 92%.

The cleavage of the acetals in step c) likewise takes place in a conventional way, in analogy to the prior art, by acid hydrolysis.

The pH is >1.5 to 7, preferably 1.6 to 2.5, according to the invention.

The acids employed are again mineral acids such as HCl, $H_2SO_4$, $H_3PO_4$ or organic acids such as acetic acid, formic acid and p-toluenesulfonic or methanesulfonic acid.

The reaction temperature is preferably between room temperature and 60° C. At the same time, the eliminated alcohol and, where appropriate, the acid are distilled out.

The OPA obtained in this way can then be further purified where appropriate, for example by extraction, washing or crystallization.

OPA is obtained in very high, halogen-free quality (>99.5 GC area %) and in very high yield of up to over 92% by the purification process of the invention. In addition, OPA purified according to the invention exhibits a constant color, and no decolorization using Tonsil or carbon is necessary. In addition, losses of yield of OPA are avoided by the process of the invention.

The process of the invention is further distinguished by a reaction time which is shortened by comparison with the prior art, thus also making a continuous procedure possible.

EXAMPLE 1

Step a)

61 g (0.25 mol) of tetrachloro-o-xylene (TCX) (purity 99%) were introduced into an autoclave, and 300 g (5 mol) of acetic acid were added. Then a solution of 44 g (1.1 mol) of NaOH and 198 g of deionized water was slowly added.

The reaction mixture was heated to 160° C. and kept at this temperature for 1 h.

Reaction pressure was 3.8-3.9 bar.

It was then cooled to 40° C. and the autoclave was emptied (606 g=525 ml of reaction solution).

2 ml of sample were taken and analyzed:

Result: 99.43 GC area % crude OPA

Extraction of crude OPA:

606 g of crude OPA solution were first mixed with 50 ml of deionized water and then extracted 4 times with 93 g of MTBE.

The organic phases were combined and then concentrated in a Rotavapor at 400-415 mbar and 34-72° C. until no further distillate passed over.

54 g of residue were obtained from the evaporation.

Step b)

The entire residue from evaporation was mixed with 375 ml of methanol, and 2 ml of conc. $H_2SO_4$ were added to adjust to pH 0.5.

After 2 hours at 50° C., 10 ml of 50% strength NaOH were added. The reaction mixture was then concentrated in a Rotavapor and subsequently mixed with 175 ml of deionized water and extracted 3× with 80 ml of MTBE at 25° C.

The organic phases were combined and concentrated in a Rotavapor.

Final weight 42.4 g

The crude acetal was distilled at a bath temperature of 135-140° C., bottom temperature of 113-114° C. and overhead temperature of 110-111° C. The pressure was 8 to 10 mbar.

Final weight: 41.2 g of OPA dimethoxy acetal (91% of theory)

Step c) OPA dimethoxy acetal cleavage:

200 g of OPA dimethoxy acetal were added to 500 g of deionized water which was adjusted to pH 2.0 with sulfuric acid, and the pressure was reduced to about 150 mbar. The heating was then started. Collection of the distillate was started at a bottom temperature of 53° C. and 155 mbar. A total of 270 ml of distillate was obtained. IPC-GC analysis of the organic phase after 4 h revealed 99.89 area % OPA.

After addition of 500 ml of DIPE, the OPA was extracted at 50° C. After phase separation, the organic phase was washed 2× with 100 ml of deionized water each time.

The washed, pale yellow-colored organic solution was heated to reflux and the water remaining in the org. phase was removed azeotropically under atmospheric pressure.

A total of 9.5 ml of water was obtained.

Subsequently, the slow cooling was started. Crystallization of OPA started at 42° C. It was cooled further to 15° C.

The crystallized OPA was filtered off through a G-2 frit, washed with 150 ml of DIPE and dried in vacuo at 40-45° C. overnight. 91.5 g of dry OPA with a content of >99.8% and 450 ml of mother liquor were isolated. The yield was 61.5% of theory.

The remaining OPA from 100% of theory was present in the mother liquor, the water from the cleavage and the water from the washing, all of which could be reemployed in the next deacetalization batch owing to the high purity and pale color of the solutions. A quantitative deacetalization was thus possible.

The invention claimed is:

1. A process for preparing high-purity, halogen-free o-phthalaldehyde, which comprises:
   a) hydrolyzing tetrahalo-o-xylene at a temperature of 155-160° C. and a pressure of from 2 to 5 bar, optionally in the presence of a phase-transfer catalyst, to o-phthalaldehyde,
   b) converting the o-phthalaldehyde in an acidic alcoholic solution at a temperature of from 0 to the reflux temperature into the corresponding dialkoxyphthalane and, subsequently,
   c) cleaving acetals by acid hydrolysis at a pH between 1.5 to 7, resulting in high-purity, halogen-free o-phthalaldehyde.

2. The process as claimed in claim 1, wherein step a) is carried out in a $C_1$-$C_4$ carboxylic acid in the presence of a base and water.

3. The process as claimed in claim 2, wherein the amount of carboxylic acid employed is between 4 to 20 mole equivalents based on tetrahalo-o-xylene.

4. The process as claimed in claim 1, wherein step b) takes place at a pH of between 0 and 3.

5. The process as claimed in claim 1, wherein step c) takes place at a pH of between 1.6 and 2.5.

* * * * *